(12) United States Patent
Smith et al.

(10) Patent No.: US 11,845,707 B2
(45) Date of Patent: Dec. 19, 2023

(54) PROCESSES AND SYSTEMS FOR C3+ MONOOLEFIN CONVERSION

(71) Applicant: ExxonMobil Chemical Patents Inc., Baytown, TX (US)

(72) Inventors: Rodney S. Smith, Edinburgh (GB); Roshni Jindal, Singapore (SG); Julie D. Hietpas, Le Havre (FR)

(73) Assignee: ExxonMobil Chemical Patents Inc., Baytown, TX (US)

(*) Notice: Subject to any disclaimer, the term of this patent is extended or adjusted under 35 U.S.C. 154(b) by 29 days.

(21) Appl. No.: 17/611,342

(22) PCT Filed: Jun. 10, 2020

(86) PCT No.: PCT/US2020/036977
§ 371 (c)(1),
(2) Date: Nov. 15, 2021

(87) PCT Pub. No.: WO2020/252007
PCT Pub. Date: Dec. 17, 2020

(65) Prior Publication Data
US 2022/0251003 A1    Aug. 11, 2022

Related U.S. Application Data

(60) Provisional application No. 62/860,580, filed on Jun. 12, 2019.

(30) Foreign Application Priority Data

Oct. 31, 2019   (EP) .................................... 19206401

(51) Int. Cl.
*C07C 2/28*    (2006.01)
*C07C 2/86*    (2006.01)
(Continued)

(52) U.S. Cl.
CPC ............... *C07C 2/28* (2013.01); *C07C 2/864* (2013.01); *C07C 1/20* (2013.01); *C07C 1/24* (2013.01); *C07C 2/08* (2013.01); *C07C 2531/10* (2013.01)

(58) Field of Classification Search
None
See application file for complete search history.

(56) References Cited

U.S. PATENT DOCUMENTS 4,826,507 A * 5/1989 Harandi .................. C07C 41/06
568/699
4,830,635 A   5/1989 Harandi et al.
(Continued)

FOREIGN PATENT DOCUMENTS

RU    2 271 349        3/2006
RU    2271349 C1  *   3/2006

OTHER PUBLICATIONS

Google Patents translation of RU2271349C1. (Year: 2006).*

*Primary Examiner* — Ali Z Fadhel

(57) ABSTRACT

Processes and systems for $C_{3+}$ monoolefin conversion. In some examples, the process can include reacting a first mixture that includes $C_{3+}$ monoolefins and a first oxygenate to produce a first effluent that includes a first ether and <1 wt. % of any first di-$C_{3+}$ olefin. A first product that includes the first ether and a first byproduct that includes at least a portion of any first di-$C_{3+}$ olefin and unreacted $C_{3+}$ monoolefins can be separated from the first effluent. A second olefin mixture, at least a portion of the first byproduct, and a second oxygenate can be combined to produce a second mixture. The second mixture can be reacted to produce a second effluent that includes a second ether and a second di-$C_{3+}$ olefin. The reaction of the second mixture can produce a greater amount, on a mole basis, of the second di-$C_{3+}$ olefin than the second ether.

30 Claims, 2 Drawing Sheets

(51) Int. Cl.
*C07C 1/24* (2006.01)
*C07C 2/08* (2006.01)
*C07C 1/20* (2006.01)

(56) References Cited

U.S. PATENT DOCUMENTS

| | | | | |
|---|---|---|---|---|
| 5,567,860 | A | * 10/1996 | Mowry | C07C 11/02 585/324 |
| 5,714,662 | A | * 2/1998 | Vora | C07C 41/06 585/638 |
| 5,986,148 | A | * 11/1999 | Beech, Jr. | C07C 41/05 568/695 |
| 6,005,150 | A | * 12/1999 | Vora | C07C 41/06 585/329 |
| 2006/0065574 | A1 | * 3/2006 | Koskinen | C07C 41/06 208/49 |
| 2007/0100194 | A1 | * 5/2007 | Pyhalahti | C07C 7/17 585/733 |
| 2015/0126699 | A1 | 5/2015 | Yarrison et al. | |

* cited by examiner

PROCESSES AND SYSTEMS FOR C3+ MONOOLEFIN CONVERSION

CROSS-REFERENCE TO RELATED APPLICATIONS

This application is a US national phase application of PCT Application Serial No. PCT/US2020/036977 having a filing date of Jun. 10, 2020, which claims priority to and the benefit of U.S. Provisional Application No. 62/860,580 having a filing date of Jun. 12, 2019 and European Patent Application No. 19206401.2 having a filing date of Oct. 31, 2019, the disclosures of all of which are incorporated herein by reference in their entireties.

FIELD

Embodiments disclosed herein generally relate to processes and systems for $C_{3+}$ monoolefin conversion. More particularly, such embodiments relate to processes and systems for the conversion of one or more $C_{3+}$ monoolefins to di-$C_{3+}$ olefins, oligomers of $C_{3+}$ olefins, polymers of $C_{3+}$ olefins, $C_{4+}$ aldehydes, $C_{4+}$ carboxylic acids, and/or $C_{4+}$ oxygenates.

BACKGROUND $C_{3+}$ monoolefins, e.g., $C_{4+}$ iso-olefins, can be used to produce many useful products such as di-$C_{4+}$ olefins and $C_{5+}$ oxygenates. In one example, isobutylene can be used to make diisobutylene that can be used as a fuel blending component. In another example, isobutylene can be used to make methyl tert-butyl ether that can be used as an industrial solvent and/or as a fuel blending component. In another example, isobutylene itself can be used as an intermediate to synthesize a number of different products, e.g., butyl rubber.

It has been observed that the relative commercial demand for $C_{4+}$ iso-olefins, di-$C_{4+}$ olefins, e.g., diisobutylene, and $C_{5+}$ oxygenates, e.g., methyl tert-butyl ether, can significantly vary in response to gasoline blendstock octane requirements and isobutylene demand for use in producing butyl rubber and/or for spot commodity markets. Current processes generally have one or more drawbacks, e.g., a product purity is too low and/or the ability to adjust the relative quantities of products in response to market demand is limited. For example, the methyl tert-butyl ether product can contain an undesirable amount of methyl sec-butyl ether.

There is a need, therefore, for improved processes and systems for converting one or more $C_{3+}$ monoolefins to one or more of: di-$C_{3+}$ olefins, oligomers of $C_{3+}$ olefins, polymers of $C_{3+}$ olefins, $C_{4+}$ aldehydes, $C_{4+}$ carboxylic acids, and $C_{4+}$ oxygenates.

SUMMARY

Processes and systems for $C_{3+}$ monoolefin conversion are provided. In some examples, the process can include reacting a first mixture that can include a first olefin mixture and a first process fluid to produce a first effluent that can include a first ether and unreacted first olefin mixture. The first olefin mixture can include ≥1 wt. % of a first $C_{3+}$ monoolefin. The first process fluid can include ≥1 wt. % of a first oxygenate. The first effluent can include <1 wt. % of a first di-$C_{3+}$ olefin or can be free of any first di-$C_{3+}$ olefin. A first product and a first byproduct can be separated from the first effluent. The first product can include at least a portion of the first ether. The first byproduct can include at least a portion of any first di-$C_{3+}$ olefin and at least a portion of the unreacted first olefin mixture. A second olefin mixture, at least a portion of the first byproduct, and a second process fluid can be combined to produce a second mixture. The second olefin mixture can include ≥1 wt. % of a second $C_{3+}$ monoolefin. The second process fluid can include ≥1 wt. % of a second oxygenate. The second mixture can be reacted to produce a second effluent that can include a second di-$C_{3+}$ olefin and a second ether. The reacting of the second mixture can produce a greater amount, on a mole basis, of the second di-$C_{3+}$ olefin than the second ether.

In other examples, the process for $C_{3+}$ monoolefin conversion can include combining a first olefin mixture and a first process fluid to produce a first mixture. The first olefin mixture can include ≥1 wt. % of a first $C_{3+}$ monoolefin. The first process fluid can include ≥1 wt. % of a first alcohol. The first mixture can be reacted in the presence of a first catalyst to produce a first effluent that can include a first ether and unreacted first olefin mixture. The first effluent can include <1 wt. % of a first di-$C_{3+}$ olefin or can be free of any first di-$C_{3+}$ olefin. A first product and a first byproduct can be separated from the first effluent. The first product can include at least a portion of the first ether. The first byproduct can include at least a portion of any first di-$C_{3+}$ olefin and at least a portion of the unreacted first olefin mixture. A second olefin mixture, at least a portion of the first byproduct, and a second process fluid can be combined to produce a second mixture. The second olefin mixture can include ≥1 wt. % of a second $C_{3+}$ olefin. The second mixture can be reacted in the presence of a second catalyst to produce a second effluent that can include a second di-$C_{3+}$ olefin, a second ether, unreacted first olefin mixture, and unreacted second olefin mixture. The reacting of the second mixture can produce a greater amount, on a mole basis, of the second di-$C_{3+}$ olefin than the second ether. The second effluent and a third process fluid can be combined to produce a third mixture. The third process fluid can include ≥1 wt. % of a second alcohol. The third mixture can be reacted in the presence of a third catalyst to produce a third effluent that can include a third ether, a third di-$C_{3+}$ olefin, unreacted first olefin mixture, and unreacted second olefin mixture. A second product and a recycle can be separated from the third effluent. The second product can include at least a portion of any first di-$C_{3+}$ olefin, at least a portion of the second di-$C_{3+}$ olefin, and at least a portion of the third di-$C_{3+}$ olefin. The recycle can include at least a portion of the second ether and at least a portion of the third ether. The second process fluid can include ≥1 wt. % of the recycle.

In some examples, a system for $C_{3+}$ monoolefin conversion can include a first reactor, a first separator, and a second reactor. The first reactor can include a first catalyst disposed therein and can be configured to react a first mixture that can include a first olefin mixture and a first process fluid in the presence of the first catalyst to produce a first effluent that can include a first ether and unreacted first olefin mixture. The first olefin mixture can include ≥1 wt. % of a first $C_{3+}$ monoolefin. The first process fluid can include ≥1 wt. % of a first oxygenate. The first effluent can include <1 wt. % of a first di-$C_{3+}$ olefin or can be free of any first di-$C_{3+}$ olefin. The first separator can be configured to separate a first product and a first byproduct from the first effluent. The first product can include at least a portion of the first ether. The first byproduct can include at least a portion of any first di-$C_{3+}$ olefin and at least a portion of the unreacted first olefin mixture. The second reactor can include a second catalyst disposed therein and can be configured to react a second mixture that can include a second olefin mixture, at least a portion of the first byproduct, and a second process fluid in the presence of the second catalyst to produce a second effluent that can include a second ether and a second di-$C_{3+}$ olefin. The second olefin mixture can include ≥1 wt. % of a second $C_{3+}$ monoolefin. The second process fluid can include ≥1 wt. % of a second oxygenate. The reacting of the second reaction mixture can produces a greater amount, on a mole basis, of the second di-$C_{3+}$ olefin than the second ether.

In other examples, a process for $C_{3+}$ monoolefin conversion can include separating a first olefin mixture and a second olefin mixture from a raffinate that can include a mixture of isobutylene, but-1-ene, cis-β-butylene, trans-β-butylene, n-butane, and isobutane. The first olefin mixture and the second olefin mixture can have substantially the same composition. Methanol can be combined with the first olefin mixture to produce a first mixture. The first mixture can be reacted in the presence of a first catalyst that can include a first cation exchange resin to produce a first effluent that can include a first methyl tert-butyl ether and unreacted first olefin mixture. The first effluent can include <1 wt. % of any first diisobutylene or can be free of any first diisobutylene. A first product and a first byproduct can be separated from the first effluent. The first product can include ≥98 wt. % of the first methyl tert-butyl ether. The first byproduct can include at least a portion of any first diisobutylene and unreacted first olefin mixture. The second olefin mixture, the first byproduct, and a recycle that can include methyl tert-butyl ether can be combined to produce a second mixture. The second mixture can be reacted in the presence of a second catalyst that can include a second cation exchange resin to produce a second effluent that can include a second methyl tert-butyl ether, a second diisobutylene, unreacted first olefin mixture, and unreacted second olefin mixture. The reacting of the second mixture can produce a greater amount, on a mole basis, of the second diisobutylene than the second methyl tert-butyl ether. Methanol can be combined with the second effluent to produce a third reaction mixture. The third reaction mixture can be reacted in the presence of a third catalyst that can include a third cation exchange resin to produce a third effluent. A second byproduct and a fourth effluent can be separated from the third effluent. The second byproduct can include but-1-ene, cis-β-butylene, trans-β-butylene, n-butane, and isobutane. A second product, a third product, and the recycle can be separated from the fourth effluent. The second product can include ≥60 wt. % of diisobutylene. The third product can include oligomers of order 3 produced from one or more of isobutylene, bute-1-ene, cis-β-butylene, and trans-β-butylene.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
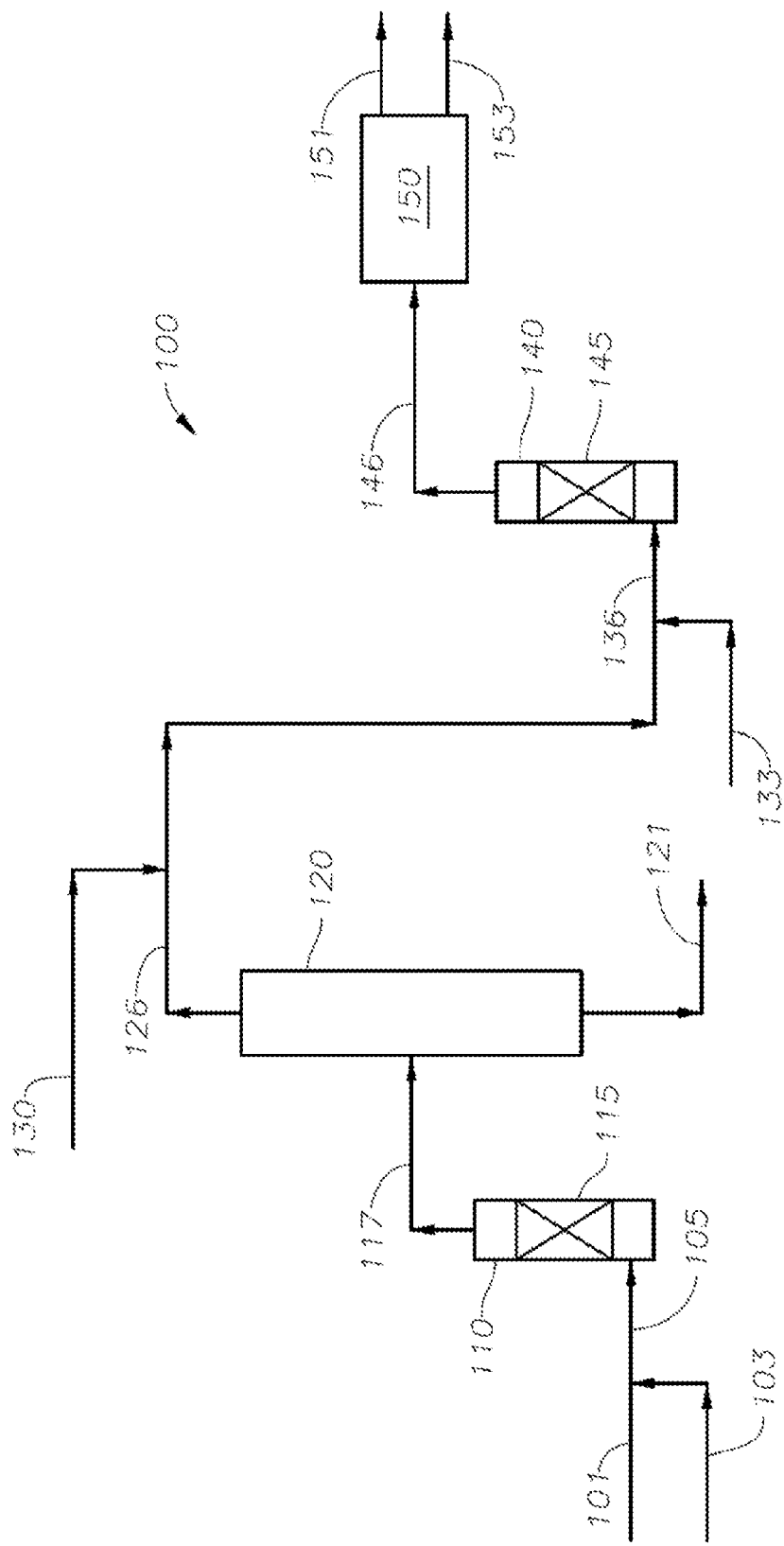
FIG. 1 depicts a schematic of an illustrative system for converting a first mixture that includes one or more $C_{3+}$ monoolefins in a first reactor to a first effluent that includes one or more oxygenates and for converting a second mixture that includes one or more $C_{3+}$ monoolefins in a second reactor to a second effluent that includes monounsaturated oligomers of order 2 of $C_{3+}$ olefins, according to one or more embodiments described.

It is to be understood that the following disclosure describes several exemplary embodiments for implementing different features, structures, and/or functions of the invention. Exemplary embodiments of components, arrangements, and configurations are described below to simplify the present disclosure; however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. Moreover, the exemplary embodiments presented below can be combined in any combination of ways, i.e., any element from one exemplary embodiment can be used in any other exemplary embodiment, without departing from the scope of the disclosure.

The process can include converting one or more $C_{3+}$ monoolefins to one or more of: monounsaturated oligomers of order 2 of $C_{3+}$ olefins ("di-$C_{3+}$ olefins"), other oligomer(s) of $C_{3+}$ olefin(s), polymer(s) of $C_{3+}$ olefin(s), $C_{4+}$ aldehyde(s), $C_{4+}$ carboxylic acid(s), and $C_{4+}$ oxygenate(s). For example, the process can include producing one or more $C_{4+}$ oxygenates and one or more di-$C_{3+}$ olefins from one or more mixtures that can include, but are not limited to, one or more $C_{3+}$ monoolefins and one or more oxygenates. In a preferred embodiment, the process can produce diisobutylene and methyl tert-butyl ether from one or more mixtures that include isobutylene and methanol.

In some examples, a first mixture that includes a first olefin mixture and a first process fluid can be reacted to produce a first effluent that can include a first ether and unreacted first olefin mixture. The first olefin mixture can include ≥1 wt. % of a first $C_{3+}$ monoolefin and the first process fluid can include ≥1 wt. % of a first oxygenate. In some examples, the first mixture can be reacted under conditions sufficient to produce the first effluent that includes the first ether and <5 wt. %, <4 wt. %, <3 w. %, <2 wt. %, <1 wt. %, <0.7 wt. %, <0.5 wt. %, <0.3 wt. %, or <0.1 wt. % of a first di-$C_{3+}$ olefin. In some examples, the first mixture can be reacted under conditions sufficient to produce the first effluent that includes the first ether and is free of any first di-$C_{3+}$ olefin. A first product and a first byproduct can be separated from the first effluent. The first product can include at least a portion of the first ether and the first byproduct can include at least a portion of any first di-$C_{3+}$ olefin and at least a portion of the unreacted first olefin mixture.

A second mixture that includes a second olefin mixture, a second process fluid, and at least a portion of the first byproduct can be reacted to produce a second effluent that can include a second ether, a second di-$C_{3+}$ olefin, and unreacted first olefin mixture, unreacted second olefin mixture, or unreacted first olefin mixture and unreacted second olefin mixture. The second olefin mixture can include ≥1 wt. % of a second $C_{3+}$ monoolefin and the second process fluid can include ≥1 wt. % of a second oxygenate. The second mixture can be reacted under conditions sufficient to produce a greater amount, on a mole basis, of the second di-$C_{3+}$ olefin than of the second ether. In some examples, the second effluent can include ≥1 wt. %, ≥2 wt. %, ≥4 wt. %, ≥6 wt. %, ≥8 wt. %, ≥10 wt. %, or ≥12, wt. % of the second di-$C_{3+}$ olefin based on the weight of the second effluent.

A second product and a second byproduct can be separated from the second effluent. The second product can include at least a portion of any first di-$C_{3+}$ olefin and at least a portion of the second di-$C_{3+}$ olefin. The second byproduct can include at least a portion of any unreacted first olefin mixture, at least a portion of any unreacted second olefin mixture, and at least portion of any unreacted first oxygenate and/or at least a portion of any unreacted second oxygenate.

It has been discovered that by reacting the first mixture to produce the first effluent having the first ether and <5 wt. %, e.g., <3 wt. %, <1 wt. %, or <0.5 wt. % of the first di-$C_{3+}$ olefin, combining the first byproduct with the second olefin mixture and the second process fluid to produce the second mixture, and reacting the second mixture to produce the second effluent under conditions sufficient to produce a greater amount, on a mole basis, of the second di-$C_{3+}$ olefin than the second ether allows for separation of the first product that includes the first ether having a significantly greater purity as compared to carrying the process out in reverse. More particularly, if the first mixture is reacted to produce a comparative first effluent having a molar ratio of ether to di-$C_{3+}$ olefin of <1, a first comparative byproduct containing unreacted first olefin mixture is mixed with the second olefin mixture and the second process fluid to produce a comparative second mixture that is reacted to produce a comparative second effluent having a molar ratio of ether to di-$C_{3+}$ olefin of ≥1, a comparative second product containing the ether separated from the comparative second effluent would contain a significantly greater amount of undesired impurities as compared to the first product containing the first ether produced according to the process disclosed herein. Prior to carrying out the process disclosed herein, it was not expected that the process disclosed herein would produce a first product containing the ether with a greater purity as compared to carrying out the process in reverse.

It has been observed that the reduction in the amount of contaminants in the first product can be reduced by 50%, >60%, >65%, >70%, >75%, >80%, >85%, or more as compared to the comparative first product described above. In some examples, the first product can include ≥98 wt. %, ≥98.05 wt. %, ≥98.1 wt. %, or ≥98.15 wt. % of the first ether, based on a total weight of the first product. In other examples, the first product can include ≥98 wt. %, ≥98.1 wt. %, or ≥98.15 wt. % of the first ether and ≤2 wt. %, ≤1.8 wt. %, or ≤1.6 wt. % of methyl sec-butyl ether, based on the total weight of the first product. If the first di-$C_{3+}$ olefin is diisobutylene, a preferred first ether produced according to the processes disclosed herein can be methyl tert-butyl ether and the primary or undesired contaminant could be methyl sec-butyl ether. In this specific example the first product can include ≥98 wt. % of methyl tert-butyl ether and <2 wt. % of methyl sec-butyl ether, based on the total weight of the first product. In another examples of this specific example the first product can include ≥98.15 wt. % of methyl tert-butyl ether and <1.6 wt. % of methyl sec-butyl ether, based on the total weight of the first product. In direct contrast, if the process were carried out in reverse, the second comparative product containing methyl tert-butyl ether would contain <98 wt. % of methyl tert-butyl ether and ≥1.6 wt. % of methyl sec-butyl ether based on the total weight of the first product. An ether product containing ≥98 wt. % of methyl tert-butyl ether is significantly more advantageous than an ether product containing <98 wt. % of methyl tert-butyl ether because industry specifications often require a methyl tert-butyl ether product that contains ≥98 wt. % of methyl tert-butyl ether.

In some examples, the process can produce ethers, e.g., methyl tert-butyl ether, and the di-$C_{3+}$ olefins, e.g., diisobutylene, in a broad molar ratio. In some examples, the process can produce the ether and the di-$C_{3+}$ olefin at a molar ratio of about 0.01:1, about 0.1:1, about 0.5:1, or about 1:1 to about 10:1, about 50:1, about 75:1, about 100:1, about 125:1, about 150:1, about 175:1, or about 200:1. As such, the process and system disclosed herein can readily be adjusted or otherwise modified to produce a greater amount of $C_{4+}$ ether relative to the di-$C_{3+}$ olefin as demand for the $C_{4+}$ ether increases. Likewise, the process and system disclosed herein can readily be adjusted or otherwise modified to produce a greater amount of di-$C_{3+}$ olefin relative to $C_{4+}$ ether as demand for the di-$C_{3+}$ olefin increases.

Representative Olefin Mixtures

In some examples, the first olefin mixture and the second olefin mixture can be separated or otherwise obtained from a common or single source material that includes a mixture of olefins. The first olefin mixture and the second olefin mixture can be separated from the source material via any suitable process and/or apparatus. For example, one or more valves, one or more dividers, split feed pipes, etc. can be used to separate the first olefin mixture and the second olefin mixture from the source material. In other examples, the first olefin mixture and the second olefin mixture can be obtained from separate or different source materials. As such, the first olefin mixture and the second olefin mixture can have substantially the same composition or different compositions with respect to one another. In some examples, a first olefin mixture and a second olefin mixture obtained from different source materials can be mixed, blended, or otherwise combined with one another to produce an olefin mixture and a first olefin mixture and a second olefin mixture having substantially the same composition can be separated therefrom.

The first olefin mixture and the second olefin mixture can each include ≥1 wt. % of $C_{3+}$ monoolefins based on the weight of the first olefin mixture or the weight of the second olefin mixture, respectively. In some examples, the first olefin mixture and the second olefin mixture can each include ≥1 wt. % of one or more $C_{4+}$ iso-olefins. Illustrative $C_{4+}$ iso-olefins can include, but are not limited to, 2-methylprop-1-ene (isobutylene), 3-methyl-1-butene (isopentene), 2-methylbut-2-ene (isoamylene), 4-methyl-1-pentene (isohexene), 2-methyl-2-pentene, or any mixture thereof. Other $C_{3+}$ monoolefins that can be present in the first olefin mixture and the second olefin mixture can include, but are not limited to, propylene, but-1-ene, cis-β-butylene, trans-β-butylene, 1-pentene, 1-hexene, 1-heptene, or any mixture thereof. In some examples, the first olefin mixture and the second olefin mixture can include other hydrocarbon components, such as alkanes, e.g., normal alkanes and/or isoalkanes, and/or light oxygenates.

An illustrative first olefin mixture and an illustrative second olefin mixture that each include isobutylene, but-1-ene, cis-β-butylene, and trans-β-butylene will now be described in further detail. The processes and systems disclosed herein, however, are not limited to a first olefin mixture and/or a second olefin mixture that includes $C_4$ monoolefins and this description is not intended to foreclose other embodiments within the broader scope of this disclosure.

In some examples the first olefin mixture and the second olefin mixture can each include ≥50 wt. %, ≥60 wt. %, ≥70 wt. %, ≥80 wt. %, or ≥90 wt. % of one or more $C_4$ monoolefins based on the weight of the first olefin mixture or the weight of the second olefin mixture, respectively. The $C_4$ monoolefins in the first olefin mixture and the second olefin mixture can generally be or include ≥1 wt. % of 1-butylene, ≥1 wt. % of 2-butylenes, and ≥1 wt. % of isobutylene. For example, the $C_4$ monoolefins in the first olefin mixture and the second olefin mixture can be about 1 wt. % to about 40 wt. % of 1-butylene, about 2 wt. % to about 45 wt. % of 2-butylenes; and about 1 wt. % to about 30 wt. % of isobutylene, based on the weight of $C_4$ monoolefins in the first olefin mixture or the second olefin mixture, respectively.

In some examples, in addition to the $C_4$ monoolefins, the first olefin mixture and/or the second olefin mixture can also include other hydrocarbon components, such as alkanes and/or light oxygenates. Illustrative alkanes that can be present in the first olefin mixture and/or the second olefin mixture can be or can include, but are not limited to, methane, ethane, propane, n-butane, isobutane, n-pentane, isopentane, n-hexane, isohexane, 3-methylpentane, 2,3-dimethylbutane, or any mixture thereof. Light oxygenate compounds can be or can include, but are not limited to, methanol, ethanol, n-propanol, isopropanol, n-butanol, t-butanol, diethyl ether, dimethylether ("DME"), diisopropyl ether, or any mixture thereof. In one example, the first olefin mixture and the second olefin mixture can include ≥20 wt. % of normal butylenes and ≥20 wt. % of isobutylene, and optionally can further include ≤5 wt. % of propane, ≤15 wt. % of n-butane, ≤25 wt. % of isobutane, and ≤1 wt. % of pentane, based on the weight of the first olefin mixture or the second olefin mixture. In another example, the first olefin mixture and the second olefin mixture can include about 14 wt. % to about 30 wt. % of 1-butylene, about 15 wt. % to about 40 wt. % of 2-butylenes; about 15 wt. % to about 25 wt. % of isobutylene, and one or more of: about 0.01 wt. % to about 5 wt. % of propane, about 1 wt. % to about 20 wt. % of n-butane, about 1 wt. % to about 5 wt. % of isobutane, and about 0.1 wt. % to about 1 wt. % of pentane, based on the weight of the first olefin mixture or the second olefin mixture.

As mentioned above, in some examples, the first olefin mixture and the second olefin mixture can be obtained from one or more source materials. In some examples, the source material can be produced by catalytic cracking, e.g., hydrocracking and/or fluidized catalytic cracking of one or more hydrocarbon feedstocks, and/or by hydrocarbon pyrolysis. In some examples, the source material can be separated, e.g., via distillation, from a steam cracked heavy hydrocarbon such as crude oil or a fraction thereof. In some examples, the source material can be or can include a $C_4$ raffinate, e.g., a raffinate I as defined in U.S. Pat. No. 7,473,812, produced by steam cracking a heavy oil.

Representative Process Fluids

The first process fluid and the second process fluid can be or can include any suitable oxygenate or mixture of oxygenates suitable for making the desired ethers and di-$C_{3+}$ olefins. In some examples, the first process fluid and the second process fluid can be the same or different with respect to one another. As such, the first oxygenate and the second oxygenate can be the same or different with respect to one another. In some examples, the first oxygenate and the second oxygenate can be or can include, but is not limited to, one or more alky alcohols, one or more ethers, or a mixture thereof. Illustrative alkyl alcohols can be or can include, but are not limited to, methanol, ethanol, n-propanol, n-butanol, n-amylalcohol, or a mixture thereof. Illustrative ethers can be or can include, but are not limited to, methyl tert-butyl ether, methyl sec-butyl ether, or a mixture thereof. As such, the first oxygenate and the second oxygenate can each be or include, but are not limited to, methanol, ethanol, n-propanol, n-butanol, n-amylalcohol, methyl tert-butyl ether, methyl sec-butyl ether, or a mixture thereof.

The first process fluid and the second process fluid can each include ≥1 wt. % of the first oxygenate or the second oxygenate, e.g., about 1 wt. % to about 100 wt. % of the first oxygenate or the second oxygenate, based on the weight of the first process fluid or the weight of the second process fluid. In some examples, the first process fluid can include about 10 wt. % to about 100 wt. % of a first alcohol, e.g., methanol. In other examples, the first process fluid can include ≥90 wt. %, ≥95 wt. %, ≥97 wt. %, or ≥99 wt. % of methanol. In some examples, the second process fluid can include methyl tert-butyl ether, methyl sec-butyl ether, or a mixture thereof. In some examples, the second process fluid can include ≥75 wt. %, ≥80 wt. %, ≥85 wt. %, ≥90 wt. %, ≥95 wt. %, ≥97 wt. %, or ≥99 wt. % of methyl tert-butyl ether. In other examples, the second process fluid can include about 70 wt. % to about 90 wt. % of methyl tert-butyl ether and about 5 wt. % to about 20 wt. % of methyl sec-butyl ether, based on the weight of the second process fluid.

It has been discovered that the second process fluid that can be combined with the second olefin mixture and the at least a portion of the first byproduct to produce the second mixture can be free or substantially free of any alcohol, e.g., methanol. For example, the second process fluid can be free or substantially free of any alcohol, e.g., can include <5 wt. %, <2 wt. %, or <1 wt. % of any alcohol such as methanol.

REPRESENTATIVE EMBODIMENTS

Certain embodiments for producing the first and second effluents and the first and second products, illustrated in FIGS. 1 and 2, will now be described in more detail. The invention is not limited to these embodiments and this description is not meant to foreclose other embodiments within the broader scope of the invention.

FIG. 1 depicts a schematic of an illustrative system 100 for converting a first mixture in line 105 that includes one or more $C_{3+}$ monoolefins in one or more first reactors 110 to a first effluent via line 117 that includes one or more $C_{4+}$ oxygenates and for converting a second mixture in line 136 that includes one or more $C_{3+}$ olefins in one or more second reactors 140 to produce a second effluent in line 146 that includes monounsaturated oligomers of order 2 of $C_{3+}$ olefins, according to one or more embodiments. In some examples, the first olefin mixture via line 101 and the first process fluid via line 103 can be mixed, blended, or otherwise combined to produce the first mixture in line 105 that can be introduced into one or more first reactors 110. In other examples, the first olefin mixture via line 101 and the first process fluid via line 103 can be introduced separately into the first reactor 110. The first mixture can react within the first reactor 110 to produce the first effluent that can include a first ether and unreacted first olefin mixture. In some examples, the first effluent in line 117 can include the first ether, unreacted first olefin mixture, and <5 wt. %, <3 wt. %, or <1 wt. % of a first di-$C_{3+}$ olefin. In other examples, the first effluent in line 117 can include the first ether, unreacted first olefin mixture, and can be free of any first di-$C_{3+}$ olefin. The first process fluid in line 103 can be or can include one or more first oxygenates, e.g., methanol.

In some examples, the first mixture can be reacted in the presence of a first catalyst 115 disposed within the first reactor 110 to produce the first effluent. For example, the first mixture can be reacted in the presence of a catalytically effective amount of the first catalyst 115 under catalytic conversion conditions. In some examples, the first catalyst can be or can include at least one first cation exchange resin, e.g., ≥95 wt. % of at least one first cation exchange resin based on the weight of the first catalyst. Conventional olefin conversion catalysts and conversion conditions can be utilized, though the processes and systems disclosed herein are not limited thereto. Suitable catalysts and catalytic conversion conditions can include those disclosed in U.S. Pat. Nos. 2,720,547; 4,219,678; 4,307,254; and 9,260,357. In some examples, the first catalyst 115 can include one or more perflurosulfonic acid resins, including those that are copolymers of sulfonyl fluorovinyl ethyl and fluorocarbon. Examples of such catalysts can include those disclosed in "Innovation", DuPont, Volume 4, No. 3, Spring 1973; and U.S. Pat. Nos. 3,770,567; 3,784,399; and 3,849,243.

In some examples, the first catalyst 115 can include at least one cation exchanger containing one or more sulfonic acid groups. In some examples, the cation exchanger can be in the form of a cation exchange resin. Such catalysts can be produced by polymerization or copolymerization of aromatic vinyl compounds followed by sulfonation. Suitable vinyl compounds can include, but are not limited to, styrene, vinyl toluene, vinyl naphthalene, vinyl ethylbenzene, methyl styrene, vinyl chlorobenzene, vinyl xylene, or a mixture thereof.

Although the processes and systems disclosed herein are not limited thereto, conventional processes can be utilized for producing the polymers, e.g., polymerization alone or in admixture with other monovinyl compounds, or by cross-linking with polyvinyl compounds such as one or more of divinyl benzene, divinyl toluene, divinylphenylether, etc. Conventional processes that can be used to introduce sulfonic acid groups into the vinyl aromatic polymers can include those disclosed in U.S. Pat. No. 4,307,254 and in references cited therein. In some examples, the first catalyst can include ≥50 wt. % of AMBERLYST®-35 and/or AMBERLYST® 15 (available from Rohm and Haas, Philadelphia, Pa.), e.g., ≥75 wt. % or ≥95 wt. % based on the weight of the first catalyst.

The first mixture can be reacted in the presence of the first catalyst 115 at a temperature ≥30° C., under an absolute pressure of ≥1 bar, and a liquid hourly space velocity (LHSV) of ≥1. When at least one bed of cation exchange resin catalyst is used in the first reactor 110, the conditions can include one or more of: (i) an inlet temperature of ≥30° C., e.g., about 40° C. to about 60° C. (start of run or "SOR"), rising to an inlet temperature of about 55° C. to about 75° C. (end of run or "EOR"); (ii) an outlet temperature of ≥35° C., e.g., about 40° C. to about 65° C. (SOR), rising to an outlet temperature of about 55° C. to about 85° C. (EOR); (iii) an absolute pressure of ≥1 bar, e.g., about 10 bar (absolute) to about 20 bar (absolute), and/or (iv) a liquid hourly space velocity (LHSV) of ≥1, e.g., about 2 to about 7. In some examples, the first mixture in line 105 can include about 15 wt. % to about 25 wt. % of isobutylene and about 10 wt. % to about 16 wt. % of methanol, based on the total weight of the second mixture.

The reaction in the first reactor 110 of at least a portion of the first $C_{3+}$ monoolefin with at least a portion of the first oxygenate in the first mixture can produce the first effluent that includes the first ether, unreacted first olefin mixture, and <1 wt. % of any first di-$C_{3+}$ olefin. In one example, the first $C_{3+}$ monoolefin can be or can include isobutylene and the first oxygenate can be or can include methanol. In this examples, the first effluent can include ≤1 wt. % of diisobutylene, >98 wt. % of methyl tert-butyl ether, and <2 wt. % of methyl sec-butyl ether, based on a combined weight of any diisobutylene, methyl tert-butyl ether, and methyl sec-butyl ether.

The first effluent via line 117 can be recovered from the first reactor 110 and introduced into one or more separators of a "first separation stage" 120. The first product via line 121 and the first byproduct via line 126 can be recovered from the first separation stage 120. The first separation stage 120 can include conventional separation technology, such as one or more fractionators, though the first separation stage 120 is not limited thereto. In some examples, when the first separation stage 120 includes fractional distillation, the first product can include about 20 wt. % to about 40 wt. % of the first effluent, and the first byproduct can include about 60 wt. % to about 80 wt. % of the first effluent, based on the weight of the first effluent.

In some examples, the first product in line 121 can include ether, e.g., ≥50 wt. % of methyl tert-butyl ether, based on the weight of the first product. In some examples, when the first olefin mixture in line 101 includes $C_4$ monoolefins and the first process fluid in line 103 includes methanol, the first product in line 121 can include ≥98 wt. %, ≥98.2 wt. %, ≥98.4 wt. %, ≥98.5 wt. %, ≥98.7 wt. %, or ≥99 wt. % of methyl tert-butyl ether based on the weight of the first product. In some examples, when the first olefin mixture in line 101 includes $C_4$ monoolefins and the first process fluid in line 103 includes methanol, the first byproduct in line 126 can include about 40 wt. % to about 60 wt. % of non-oligomerized $C_4$ monoolefin based on the weight of the first byproduct, where the term "non-oligomerized" means olefin that is not oligomerized in the first reactor 110.

In some examples, the second olefin mixture via line 130 and the second process fluid via line 133 can be combined with at least a portion of the first byproduct in line 126 to produce the second mixture via line 136 that can be introduced into one or more second reactors 140. In other examples, the second olefin mixture via line 130, the second process fluid via line 133, and at least a portion of the first byproduct via line 126 can be introduced separately into the second reactor 140. In other examples, two of the first byproduct in line 126, the second olefin mixture in line 130, and the second process fluid in line 133 can be combined to produce a combined mixture with the combined mixture and the uncombined feed being introduced separately to the second reactor 140. The second mixture can react within the second reactor 140 to produce the second effluent that can include a second ether and a second di-$C_{3+}$ olefin. The second mixture can be reacted under conditions that can produce a greater amount, on a mole basis, of the second di-$C_{3+}$ olefin than the second ether.

In some examples, the second mixture can be reacted in the presence of a second catalyst 145 disposed within the second reactor 140 to produce the second effluent. For example, the second mixture can be reacted in the presence of a catalytically effective amount of the second catalyst 145 under catalytic conversion conditions. In some examples, the second catalyst can be or can include at least one second cation exchange resin, e.g., ≥95 wt. % of at least one second cation exchange resin based on the weight of the second catalyst. Conventional olefin conversion catalysts and conversion conditions can be utilized, though the processes and systems disclosed herein are not limited thereto. In some examples, the second catalyst 145 can be selected from among the same catalyst as the first catalyst 115 used in the first reactor 110. In some examples, the second catalyst 145 can have substantially the same composition as the first catalyst 115.

The second mixture can be reacted in the presence of the second catalyst 145 at a temperature of ≥30° C., under an absolute pressure of ≥1 bar, and a liquid hourly space velocity (LHSV) of ≥1. When at least one bed of cation exchange resin catalyst is used in the second reactor 140, the conditions can include (i) an inlet temperature of ≥30° C., e.g., about 40° C. to about 55° C. (SOR), rising to an inlet temperature of about 45° C. to about 85° C. (EOR); (ii) an outlet temperature of ≥45° C., e.g., about 50° C. to about 75° C. (SOR), rising to an outlet temperature of about 60° C. to about 90° C. (EOR); (iii) an absolute pressure of ≥1 bar, e.g., about 10 bar (absolute) to about 20 bar (absolute), and (iv) a space velocity (LHSV) of ≥1, e.g., about 1 to about 7. In some examples, the second mixture in line 136 can include about 12 wt. % to about 21 wt. % of isobutylene, about 10 wt. % to about 15 wt. % or methyl tert-butyl ether, about 1.5 wt. % to about 3 wt. % of methyl sec-butyl ether, and ≤1 wt. % of diisobutylene based on the total weight of the second mixture.

The reaction of the second mixture within the second reactor 145 of at least a portion of the second $C_{3+}$ monoolefin in the second mixture can produce a greater amount, on a mole basis, of the second di-$C_{3+}$ olefin than the second ether. In one example, the second $C_{3+}$ monoolefin can be or can include isobutylene and the second ether can be or can include methyl tert-butyl ether. In some examples, the second effluent can also include unreacted second oxygenate, unreacted $C_{3+}$ monoolefin, and/or oligomers of order ≥3 of $C_{3+}$ olefins.

Referring again to FIG. 1, the second effluent via line 146 can be conducted away from the second reactor 140 to one or more separators of a second separation stage 150 that can include one or more separators for separating a second product via line 151 and one or more second byproducts via line 153 from the second effluent. The second product can include at least a portion of the di-$C_{3+}$ olefin and at least a portion of the second ether in the second effluent. In some examples, the separation stage 150 can utilize conventional separation technology, such as one or more fractionators, though the separation stage 150 is not limited thereto. In some examples, the separation stage 150 can utilize one or more catalytic distillation columns, though the separation stage 150 is not limited thereto. When the separation stage 150 includes fractional distillation, the second product can include, e.g., ≥20 wt. % of the second effluent (such as ≥50 wt. %) and the second byproduct can include, e.g., ≤80 wt. % of the second effluent, based on the weight of the second effluent. It has been observed that the presence of methyl tert-butyl ether in the second reactor 140 (such as when at least a portion of the methyl tert-butyl ether obtained from one or more of the first product, the second effluent in line 146, the second product in line 151 that can be introduced or otherwise conducted to the second reactor 140), can lessen the amount of oligomers of order ≥3 of $C_{3+}$ olefin produced in the second reactor 140 by shifting chemical equilibrium in favor of di-$C_{3+}$ olefin production. As such, in some examples methyl tert-butyl ether or a methyl tert-butyl ether containing feed can be introduced to the second reactor 140, e.g., as the second process fluid or as a component of the second process fluid or independently introduced to the second reactor 140.

The second product in line 151 can generally include ≥50 wt. %, e.g., ≥75 wt. % or ≥90 wt. %, of the di-$C_{3+}$ olefin and ether in the second effluent based on the weight of the di-$C_{3+}$ olefin and ether in the second effluent. The second product via line 151 can be conducted away from the second separation stage 150, e.g., storage, blending with gasoline to increase an octane number of the gasoline and/or oxygenate content, or further processing.

In some examples, when the second olefin mixture includes $C_{4+}$ monoolefins, the amount of normal $C_{4+}$ monoolefins and/or the amount of iso-$C_{4+}$ monoolefin converted in the second reactor 140 can make it desirable to increase the amount of $C_{4+}$ monoolefin available for conversion in the first reactor 110 or vice versa. The amount of $C_{4+}$ monoolefin introduced via lines 101 and 130 can be controlled or adjusted so that the desired amount of ether and di-$C_{4+}$ monoolefin is produced in the first reactor 110 and the second reactor 140. In some examples, a mass ratio of the amount of the first olefin mixture conducted via line 101 to the first reactor 110 to the amount of the second olefin mixture conducted via line 130 to the second reactor 140 can be about 0.1:1, about 0.2:1, about 0.5:1, about 1:1, or about 2:1 to about 3:1, about 5:1, about 7:1, or about 10:1. In some examples, the mass ratio of the amount of the first olefin mixture conducted via line 101 to the first reactor 110 to the amount of the second olefin mixture conducted via line 130 to the second reactor 140 can be ≥1:1, e.g., about 1.5:1 to about 2:1 or about 1.5:1 to about 3:1. Adjusting or otherwise controlling the amount of the first olefin mixture and the second olefin mixture introduced to the first reactor 110 and the second reactor 140, respectively, allows for varying the amount of $C_{4+}$ oxygenate(s) and the amount of di-$C_{3+}$ olefins produced via the process, e.g. to provide a $C_{4+}$ oxygenate to di-$C_{3+}$ olefin weight ratio in the range of about 0.01:1 to about 100:1, such as about 0.1:1 to about 10:1.

Figure 2:
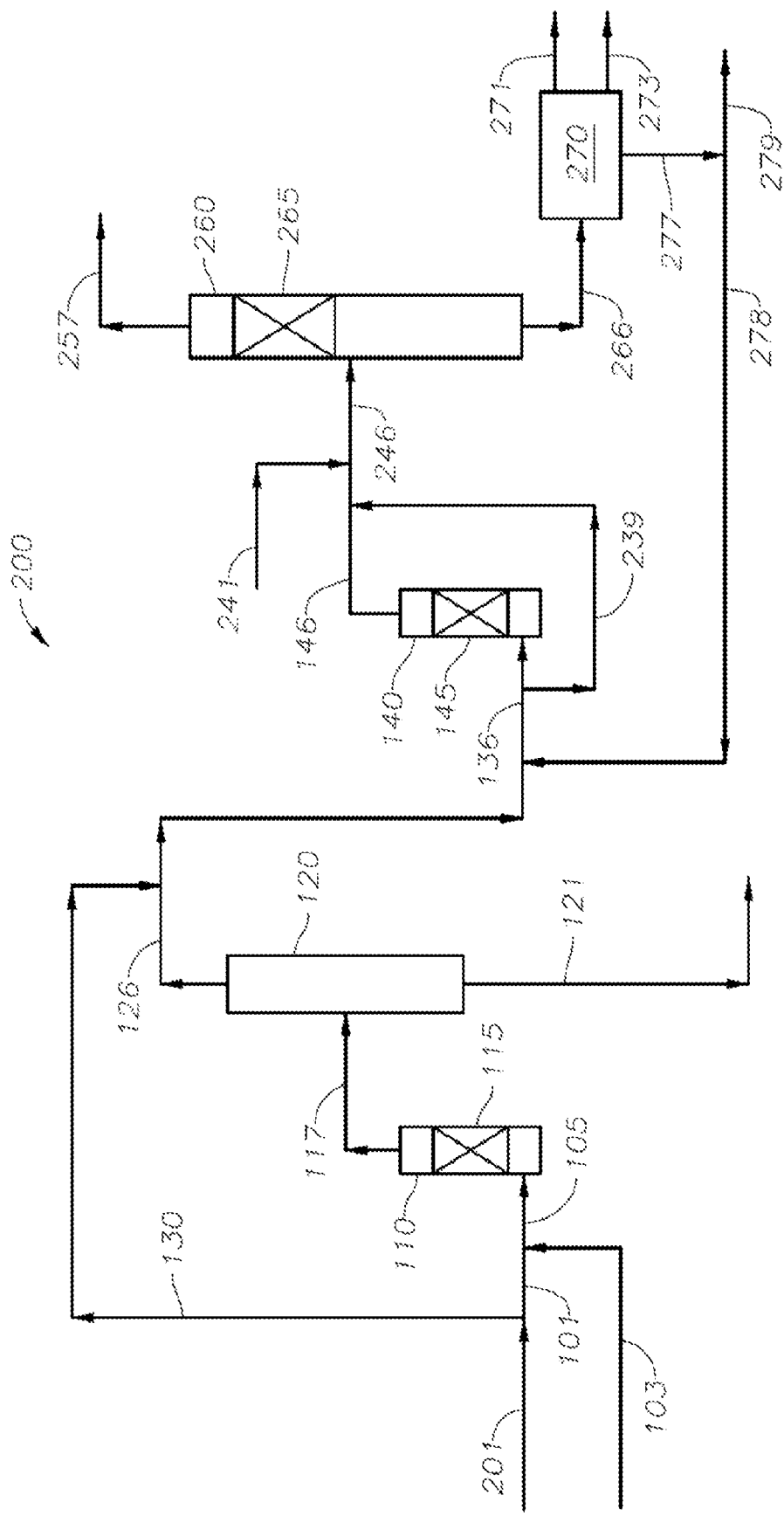
FIG. 2 depicts a schematic of another illustrative system that is similar to the system depicted in FIG. 1, but the system further includes a reactor-separator to further convert unreacted $C_{3+}$ monoolefins to additional monounsaturated oligomers of order 2 of $C_{3+}$ olefins and/or additional oxygenate(s), according to one or more embodiments described.

FIG. 2 depicts a schematic of another illustrative system 200 that is similar to the system 100 depicted in FIG. 1, but the system 200 further includes a reactor-separator unit 260, e.g., catalytic distillation column, to further convert at least a portion of any unreacted $C_{3+}$ monoolefins in the second effluent to additional mono-unsaturated oligomers of order 2 of $C_{3+}$ olefins and/or additional oxygenate(s), according to one or more embodiments. As shown in FIG. 2, an olefin source in line 201 can supply the first olefin mixture in line 101 and the second olefin mixture in line 130. A first process fluid via line 103 can be mixed, blended, or otherwise combined with the first olefin mixture in line 101 to produce the first mixture via line 105. In some examples, valves or other dividing means can be used to adjust or otherwise control the relative amount of the first and second olefin introduced into lines 101 and 131, respectively.

The first reactor 110, the first separation stage 120, and the second reactor 140 can provide the first product via line 121, the first byproduct via line 126, and the second effluent via line 146, as described above with reference to FIG. 1. As shown in FIG. 2, at least a portion of a recycle in line 277 via line 278 can be mixed, blended, or otherwise combined with the second olefin mixture and at least a portion of the first byproduct to produce the second mixture in line 136. In this example, the recycle in line 278 can be or can make up at least a portion of the second process fluid that can be combined with the second olefin mixture and the first byproduct to produce the second mixture. In some examples, at least a portion of the second mixture in line 136 can be bypassed via line 239 around the second reactor 140 and mixed, blended, or otherwise combined with the second effluent.

Bypassing a portion of the second mixture around the second reactor can adjust a concentration of the $C_{3+}$ monoolefin(s), e.g., $C_{4+}$ iso-olefin, in the second effluent. In some examples, maintaining a predetermined amount of certain $C_{3+}$ monoolefins, e.g., iso-olefin(s) relative to the amount of normal $C_{3+}$ monoolefin(s), e.g., 1-butylene, in the second effluent can reduce an amount of the normal $C_{3+}$ monoolefin(s), e.g., 1-butylene, that can be converted to one or more undesirable contaminants, e.g., methyl sec-butyl ether, within the reactor-separator unit 260. In some examples, when the second mixture includes $C_{4+}$ monoolefins, the amount of the second mixture bypassed via line 239 and introduced to the second effluent can be sufficient to provide a molar ratio of isobutylene to 1-butylene in the second effluent in line 146 of $\geq 10$, $\geq 20$, $\geq 30$, or $\geq 40$. In some examples, the second effluent can include about 0.2 wt. %, about 0.5 wt. %, about 1 wt. %, or about 1.5 wt. % to about 2 wt. %, about 2.5 wt. %, about 3 wt. %, about 5 wt. %, or about 10 wt. % of isobutylene based on the total weight of the second effluent.

The reactor-separator unit 260 can include one or more third catalysts 265 disposed therein. In some examples, the second effluent via line 146 can be introduced into the reactor-separator unit 260 and at least a portion of any unreacted $C_{3+}$ monoolefin, e.g., $C_{4+}$ iso-olefin and/or at least a portion of any unreacted first process fluid, e.g., methanol, can be converted to additional ether and/or additional di-$C_{3+}$ olefin to produce a third effluent within the reactor-separator unit 260. In other examples, a third process fluid via line 241 can be mixed, blended, or otherwise combined with the second effluent to produce a third mixture in line 246. The third process fluid can include $\geq 1$ wt. % of a third oxygenate, e.g., a second alcohol. In some examples, the third process fluid can include $\geq 65$ wt. % of the second alcohol, e.g., methanol. In some examples, the third oxygenate can be or can include methanol, ethanol, n-propanol, n-butanol, n-amylalcohol, or any mixture thereof.

The second effluent via line 146 or the third mixture via line 246 can be introduced into the reactor-separator unit 260 below, above, and/or directly into the space that includes the third catalyst 265. A second byproduct via line 267 that includes unreacted $C_{3+}$ monoolefin and unreacted oxygenate from the first and/or second process fluids, and/or other light hydrocarbons can be separated from the third effluent and recovered from the reactor-separator unit 260. A fourth effluent via line 266 can be can be recovered from the reactor-separator unit 260.

In some examples, the reaction conditions within the reactor-separator 260 can include, e.g., a gauge pressure of about 0 bar, about 2 bar, or about 5 bar to about 10 bar, about 20 bar, or about 30, and a temperature of about 0° C., about 10° C., about 25° C., or about 50° C. to about 100° C., about 125° C., or about 160° C. In some examples, the reactor-separator 260 can include a catalytically effective amount of at least one conversion catalyst, e.g., at least one cation resin containing at least one sulfonic acid group. In some examples, the third catalyst can be or can include at least one third cation exchange resin, e.g., $\geq 95$ wt. % of at least one third cation exchange resin based on the weight of the third catalyst. In some examples, suitable conversion catalysts can be produced by the polymerization or copolymerization of aromatic vinyl compounds followed by sulfonation. The third catalyst 265 can be substantially the same as the first catalyst 115 and the second catalyst 145 that can disposed within the first reactor 110 and the second reactor 140, respectively. Although the third catalyst 265 in the reactor-separator 260 can be located above, at, or below the location where the second effluent via line 146 or the third mixture via line 246 enters the reactor-separator 260, a majority of the third catalyst 265, e.g., >50 wt. % or $\geq 75$ wt. % of the catalyst based on the weight of the third catalyst 265 in the reactor-separator 260, can be located above the location where line 146 or 246 enters the reactor-separator 260. For example, $\geq 90$ wt. % or even substantially all of the catalyst can be located above the location where line 146 or 246 enters the reactor-separator 260.

When the second effluent in line 146 or the third mixture in line 246 includes $C_4$ monoolefins and methanol, the reactor-separator 260 can produce a third effluent that includes additional di-$C_4$ olefin and additional methyl tert-butyl ether, relative to the second effluent in line 146 or the third mixture in line 246. The separation functionality of the reactor-separator 260 can be used to separate from the third effluent the second byproduct (overhead stream) via line 267 that is relatively free of isobutylene, e.g., includes $\leq 1$ wt. %, based on the weight of the second byproduct and the fourth effluent via line 266 that includes diisobutylene and methyl tert-butyl ether.

When the third catalyst 265 is utilized in the reactor-separator 260, the third effluent can include diisobutylene, with at least a first portion of the diisobutylene being produced in the reactor-separator 260 by reacting unreacted second process fluid and/or unreacted second olefin mixture. A second portion of the diisobutylene in the third effluent can include diisobutylene produced in the first reactor 110 and/or the second reactor 140 and conducted to the reactor-separator 260 as a component of the second effluent via line 146 or the third mixture via line 246. When the third catalyst 265 is utilized in the reactor-separator 260, the third effluent can include ether, with at least a first portion of the ether being produced in the reactor-separator 260 by reacting unreacted first process fluid, third oxygenate, unreacted first olefin mixture, and/or unreacted second olefin mixture. A second portion of the ether in the third effluent can include ether produced in the first reactor 110 and/or the second reactor 140 and conducted to the reactor-separator 260 as a component of the second effluent via line 146 or the third mixture via line 246.

It should be understood that the system 200 can include one or more stand-alone reactors and one or more stand-alone separation stages. In such a system the stand-alone reactor and the stand-alone separation stage can be similar to the first reactor 110 and/or the second reactor 140 and the stand-alone separation stage can be similar to separation stage 120. When the system 200 includes the reactor-separator 260, as depicted in FIG. 2, the reaction conditions and catalyst can be substantially the same as those disclosed in U.S. Pat. No. 4,307,254. In some examples, it can be desirable to operate the reactor-separator 260 under reflux conditions, e.g., by cooling and returning to the reactor-separator a portion of the second byproduct in line 267, as disclosed in U.S. Pat. No. 7,473,812. Since it is generally desirable to specify the size of the reactor-separator 260 vessel for operations that produce a fourth effluent via line 266 that includes a greater amount of di-$C_{3+}$ olefin and less (on a molar basis) $C_{4+}$ oxygenate, it has been found that a greater reflux ratio than is utilized in U.S. Pat. No. 7,473,812 can be used. In some examples, the reflux ratio (weight basis) can be ≥1.55, e.g., ≥1.6, such as ≥1.65, or from about 1.6 to about 2, or about 1.7 to about 1.90.

In some examples, the fourth effluent in line 266 can include ≥1 wt. % of di-$C_{3+}$ olefin, e.g., diisobutylene, based on the weight of the fourth effluent, e.g., about 20 wt. % to about 40 wt. % or about 25 wt. % to about 35 wt. %. In some examples, the fourth effluent in line 266 can include ≥1 wt. % of ether, e.g., methyl tert-butyl ether, based on the weight of the fourth effluent, e.g., about 40 wt. % to about 60 wt. % or about 45 wt. % to about 50 wt. %. In some examples, the fourth effluent in line 266 can have a non-oligomerized $C_{3+}$ monoolefin (e.g., isobutylene+normal butylenes) to di-$C_{3+}$ olefin molar ratio of ≤1, ≤0.5, ≤0.3, or ≤0.1, where the term "non-oligomerized" means olefin that is not oligomerized in the first reactor 110, the second reactor 140, or the reactor-separator 260.

In some examples, the fourth effluent in line 266 can include about 40 wt. % to about 55 wt. % of methyl tert-butyl ether, about 5 wt. % to about 10 wt. % of methyl sec-butyl ether, and about 25 wt. % to about 35 wt. % of diisobutylene based on the weight of the fourth effluent.

The fourth effluent via line 266 can be introduced to a second separation stage 270 that can include one or more separators for separating a second product via line 271, a third product via line 273, and a recycle via line 277 from the fourth effluent in line 266. In some examples, a first portion of the recycle in line 277 can be recycled via line 278 to the system 200 and a second portion of the recycle in line 277 can be conducted away from the system 200 via line 279. As shown, at least a portion of the recycle via line 278 can be mixed, blended, or otherwise combined with the second mixture in line 136. In other examples, in addition to or in lieu of combining at least a portion of the recycle with the second mixture, at least a portion of the recycle can be mixed, blended, or otherwise combined with the bypass in line 239, the second effluent in line 146, the first produce in line 121, introduced into the reactor-separator 260, or any combination thereof. In some examples, the recycle in line 278 can be combined with the second olefin in line 131 and/or the first byproduct in line 126 and can be referred to as the second process fluid.

The second product in line 271 can include about 65 wt. % to about 85 wt. % of diisobutylene, about 35 wt. % to about 15 wt. % of 2,5-dimethyl-3-hexene, and about 1 wt. % to about 8 wt. % of 1-dodecene based on a combined weight of the diisobutylene, the 2,5-dimethyl-3-hexene, and the 1-dodecene. The third product in line 273 can include about 80 wt. % to about 95 wt. % of 1-dodecene, about 0.1 wt. % to about 2 wt. % of 2,5-dimethyl-3-hexene, and about 5 wt. % to about 15 wt. % of 1-hexadecene based on a combined weight of the 1-dodecene, the 2,5-dimethyl-3-hexene, and the 1-hexdecene. The amount of recycle via line 277 can include about 75 wt. % to about 90 wt. % of methyl tert-butyl ether, about 10 wt. % to about 20 wt. % of methyl sec-butyl ether, and ≤about 2 wt. % or ≤1.5 wt. % of other compounds based on a total weight of the recycle.

Obtaining a Source Material by Pyrolysis

One example that can be used to produce the source material from which the first olefin mixture and/or the second olefin mixture can be sourced from will now be described in more detail. The processes and systems disclosed herein, however, are not to be limited to this this exemplary process for producing the source material, and the description is not meant to foreclose other methods for producing the source material within the broader scope of this disclosure.

In some examples, the source material can be produced by steam cracking of a feed comprising hydrocarbon and water (steam). One conventional steam cracking process utilizes a pyrolysis furnace that has two main sections: a convection section and a radiant section. The feed typically enters the convection section of the furnace, where the feed's hydrocarbon component is heated and vaporized by indirect contact with hot flue gas from the radiant section and by direct contact with the steam component in the feed. The steam-vaporized hydrocarbon mixture is then introduced into the radiant section where the cracking takes place. A steam-cracker product is conducted away from the pyrolysis furnace that can include a mixture of products resulting from the pyrolysis of the feed (generally products of hydrocarbon pyrolysis) and unreacted components of the feed (primarily water). At least one separation stage is generally located downstream of the pyrolysis furnace, the separation stage can be configured to separate one or more of light olefins, steam cracker naphtha, steam cracker gas oil, separation stage bottoms (e.g., primary fractionator bottoms), steam cracker tar, steam cracker coke, water, unreacted hydrocarbon components of the feed, and/or other products or fractions from the steam-cracker product. The separation stage can include, e.g., a primary fractionator. Optionally, a cooling stage can be located between the pyrolysis furnace and the separation stage.

The steam cracker feed can be produced by combining the hydrocarbon with a diluent comprising steam, e.g., at a ratio of about 0.2 kg of steam to about 4 kg of steam per kg of hydrocarbon. For example, hydrocarbon in the steam cracker feed can include ≥10 wt. %, e.g., ≥50 wt. %, such as ≥90 wt. % (based on the weight of the hydrocarbon component) of one or more of naphtha, gas oil, vacuum gas oil, crude oil, resid, or resid admixtures; including those that include ≥0.1 wt. % of asphaltenes. Suitable crude oils include, e.g., high-sulfur virgin crude oils, such as those rich in polycyclic aromatics.

When the steam cracker feed includes a heavy hydrocarbon, e.g., crude oil or fractions thereof, it can be desirable for the pyrolysis furnace to utilize at least one vapor/liquid separation device (sometimes referred to as flash pot or flash drum) integrated therewith. Such vapor/liquid separator devices are particularly suitable when the hydrocarbon in the feed includes ≥0.1 wt. % of asphaltenes based on the weight of the hydrocarbon in the feed, e.g., ≥5 wt. %.

The vapor/liquid separation device can be used to separate and conduct away at least a portion of the high molecular-weight molecules, such as asphaltenes, in the feed. Conventional vapor/liquid separation devices can be utilized, though the processes and systems disclosed herein are not limited thereto. Illustrative conventional vapor/liquid separation devices can include those disclosed in U.S. Pat. Nos. 7,138,047; 7,090,765; 7,097,758; 7,820,035; 7,311,746; 7,220,887; 7,244,871; 7,247,765; 7,351,872; 7,297,833; 7,488,459; 7,312,371; and 7,235,705. Other suitable vapor/liquid separation devices can include those disclosed in U.S. Pat. Nos. 6,632,351 and 7,578,929.

Suitable steam cracking conditions can include, e.g., exposing the feed to a temperature (measured at the radiant outlet) of ≥400° C., e.g., a temperature of about 400° C. to about 900° C., and an absolute pressure of ≥0.1 bar, for a cracking residence time period of about 0.01 second to about 5 seconds. When the feed includes a heavy hydrocarbon and about 10 wt. % to about 90 wt. % of water based on the weight of the feed, the steam cracking conditions generally include one or more of (i) a temperature in the range of about 760° C. to about 880° C.; (ii) an absolute pressure of about 1 bar to about 5 bar; and/or (iii) a residence time of about 0.1 seconds to about 2 seconds. The steam-cracker product can include ≥1 wt. % of $C_2$ to $C_4$ unsaturates (light olefin), steam cracker naphtha, and steam cracker gas oil; the relative amount of each of these generally depending on, e.g., the steam cracker's composition, pyrolysis furnace configuration, process conditions during the pyrolysis, etc. The steam-cracker product can be conducted away from the pyrolysis section, e.g., for cooling and/or separation stages.

A separation stage can generally be utilized downstream of the pyrolysis furnace (and optionally downstream of a cooling stage) for separating from the steam-cracker product one or more of light olefins, steam cracker naphtha, steam cracker gas oil, or water. Conventional separation equipment can be utilized in the separation stage, e.g., one or more flash drums, fractionators, water-quench towers, indirect condensers, etc., such as those disclosed in U.S. Pat. No. 8,083,931.

The source material can generally be separated from the steam-cracker product in the separation stage, e.g., separated from the light olefin portion of the steam-cracker product. For example, a de-butanizer can be utilized for separating a $C_4$ product from the steam-cracker product. The source material can be obtained from the $C_4$ stream by extraction that uses an extractant (e.g., a mixture of sodium hydroxide and water), with the source material generally including at least a portion of a raffinate. Conventional de-butanizing and extracting technology can be used, though the processes and systems disclosed herein are not limited thereto. In some examples, in can be desirable for the source material and first olefin mixture to contain ≤1 wt. % multi-unsaturated olefins such as butadiene (based on the weight of the source material or the first olefin mixture as the case may be), e.g., ≤0.5 wt. %. Conventional methods can be utilized to do this, but the processes and systems disclosed herein are not limited thereto. Suitable methods include those disclosed in U.S. Pat. No. 7,473,812.

When the source material is obtained from a steam-cracker product produced from a heavy hydrocarbon feed, the source material can include, e.g., ≥10 wt. % of isobutylene and ≥25 wt. % of normal butylenes with ≤10 wt. % of a combined amount of any n-butane and any $C_{5+}$ material. For example, the source material can include about 18 wt. % to about 25 wt. % of isobutylene and about 55 wt. % to about 65 wt. % normal butylenes. In some examples, the first olefin mixture and the second olefin mixture can each include at least a portion of the source material. The first olefin mixture and the second olefin mixture can have substantially the same composition as the source material, such as when the first olefin mixture and the second olefin mixture are derived from the source material by separation (e.g., absorption, distillation, or other physiochemical means) or by dividing the source material into a first portion to be utilized as the first olefin mixture and at least a second portion to be utilized as the second olefin mixture. This can be done using conventional means (e.g., valves, one or more splitters, etc.).

In some examples, an illustrative source material can include, but is not limited to, a $C_4$ olefin produced by (a) steam cracking a heavy oil, followed by (b) primary fractionation of the steam-cracker product to separate a $C_{4+}$ olefin-containing fraction, (c) depropanizing and depentanizing the $C_{4+}$ olefin-containing fraction, and then separating a raffinate that can include the $C_4$ olefin source material. For example, the source material (and the first olefin mixture and/or the second olefin mixture) can have the following composition: ≤1 wt. % of a multi-unsaturated olefin such as butadiene, ≤0.1 wt. % of methane, e.g., about 0.01 wt. % to about 0.1 wt. %; ≤0.1 wt. % of propane, e.g., about 0.01 wt. % to about 0.1 wt. %; ≤2 wt. % of isobutane, e.g., about 0.5 wt. % to about 2 wt. %; ≥10 wt. % of isobutylene, e.g., about 15 wt. % to about 25 wt. %; ≥25 wt. % of 1-butylene, e.g., about 30 wt. % to about 40 wt. %; ≥15 wt. % of trans-β-butylene, e.g., about 20 wt. % to about 30 wt. %; ≥1 wt. % of cis-β-butylene, e.g., about 2 wt. % to about 10 wt. %; and ≤10 wt. % of n-butane, e.g., about 2 wt. % to about 10 wt. %, the weight percent values are based on the weight of the source material or first olefin mixture or the second olefin mixture as the case may be.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A process for $C_{3+}$ monoolefin conversion, comprising:
providing a first mixture comprising a first process fluid and a first olefin mixture,
catalytically reacting at least a portion of the first mixture's first process fluid with at least a portion of the first mixture's first olefin mixture to produce a first effluent comprising a first ether and unreacted first olefin mixture, wherein the first olefin mixture comprises ≥1 wt. % of a first $C_{3+}$ monoolefin, wherein the first process fluid comprises ≥1 wt. % of a first oxygenate, and wherein the first effluent comprises <1 wt. % of a first di-$C_{3+}$ olefin or is free of any first di-$C_{3+}$ olefin;
separating a first product and a first byproduct from the first effluent, wherein the first product comprises at least a portion of the first ether, and wherein the first byproduct comprises at least a portion of the unreacted first olefin mixture;
combining a second olefin mixture, at least a portion of the first byproduct, and a second process fluid to produce a second mixture, wherein (i) the second olefin mixture comprises ≥1 wt. % of a second $C_{3+}$ monoolefin, and (ii) the second process fluid comprises ≥1 wt. % of a second oxygenate; and
catalytically reacting two or more of (i) at least a portion of the second mixture's second process fluid, (ii) at least a portion of the second mixture's second olefin mixture, and (iii) at least a portion of the second mixture's first byproduct to produce a second effluent comprising a second di-$C_{3+}$ olefin and a second ether, wherein the reaction produces a greater amount, on a mole basis, of the second di-$C_{3+}$ olefin than that of the second ether, wherein the second effluent further comprises unreacted first C3+ monoolefin, unreacted second C3+ monoolefin, or a mixture thereof, reacting at least a portion of any unreacted first $C_{3+}$ monoolefin, at least a portion of any unreacted second $C_{3+}$ monoolefin, or both in a third reactor to produce a third effluent comprising a third di-$C_{3+}$ olefin, a third ether;

obtaining a second product, a third product, and a recycle from the third effluent, and mixing a portion of the recycle with the first byproduct, the second olefin mixture, the second mixture, the second effluent, or a combination of two or more thereof.

2. The process of claim 1, wherein the first oxygenate comprises a first alcohol.

3. The process of claim 1, wherein the first oxygenate comprises methanol, ethanol, n-propanol, n-butanol, n-amylalcohol, or a mixture thereof.

4. The process of claim 1, wherein the first olefin mixture and the second olefin mixture each further comprise but-1-ene, cis-p-butylene, trans-R-butylene, n-butane, or a mixture thereof.

5. The process of claim 1, wherein the first ether, the second oxygenate, and the second ether each comprise methyl tert-butyl ether, and wherein the first di-$C_{3+}$ olefin and the second di-$C_{3+}$ olefin each comprise diisobutylene.

6. The process of claim 1, wherein the first product comprises ≥98 wt. % of methyl tert-butyl ether, based on the weight of the first product.

7. The process of claim 1, wherein the first mixture is reacted in the presence of a first catalyst to produce the first effluent, and wherein the second mixture is reacted in the presence of a second catalyst to produce the second effluent.

8. The process of claim 1, further comprising separating a second product and a second byproduct from the second effluent, wherein the second product comprises at least a portion of any first di-$C_3$ olefin and at least a portion of the second di-$C_3$+ olefin.

9. The process of claim 1, wherein:
the third di-C3+ olefin comprises diisobutylene,
the third ether comprises methyl tert-butyl ether, methyl sec-butyl ether, or a mixture thereof,
the second product comprises >60 wt. % of diisobutylene based on the weight of the second product;
the third product comprises >90 wt. % of one or more tri-C4+ olefins based on the weight of the third product,
the second byproduct comprises but-1-ene, cis-β-butylene, trans-β-butylene, n-butane, or a mixture thereof,
the recycle comprises methyl tert-butyl ether, methyl sec-butyl ether, or a mixture thereof, and
the second process fluid comprises a portion of the recycle.

10. The process of claim 9, wherein the second by-product comprises no greater than 1 wt % of isobutylene, based on the total weight of the second byproduct.

11. The process of claim 1, wherein the recycle comprises about 75 wt. % to about 90 wt. % of methyl tert-butyl ether based on a total weight of the recycle.

12. The process of claim 11, wherein the recycle comprises about 10 wt. % to about 20 wt. % of methyl sec-butyl ether based on a total weight of the recycle.

13. The process of claim 1, wherein the first olefin mixture and the second olefin mixture are the same.

14. The process of claim 1, wherein at least a portion of the first byproduct is supplied into the third reactor.

15. The process of claim 1, wherein:
the third reactor comprises a reactive distillation column, and a second byproduct comprising unreacted second mixture is produced from the third reactor.

16. The process of claim 1, wherein the third effluent further comprises unreacted second mixture; and the process further comprises:
separating a second byproduct comprising at least a portion of the unreacted second mixture and a fourth effluent from the third effluent; and
separating a second product, a third product, and a recycle from the fourth effluent.

17. A process for $C_{3+}$ monoolefin conversion, comprising:
combining a first olefin mixture and a first process fluid to produce a first mixture, wherein the first olefin mixture comprises ≥1 wt. % of a first $C_{3+}$ monoolefin, and wherein the first process fluid comprises ≥1 wt. % of a first alcohol;
reacting the first mixture in the presence of a first catalyst to produce a first effluent comprising a first ether and unreacted first olefin mixture, wherein the first effluent comprises <1 wt. % of a first di-$C_{3+}$ olefin or is free of any first di-$C_{3+}$ olefin;
separating a first product and a first byproduct from the first effluent, wherein the first product comprises at least a portion of the first ether, and wherein the first byproduct comprises at least a portion of the unreacted first olefin mixture;
combining a second olefin mixture, at least a portion of the first byproduct, and a second process fluid to produce a second mixture, wherein the second olefin mixture comprises ≥1 wt. % of a second $C_{3+}$ olefin;
reacting the second mixture in the presence of a second catalyst to produce a second effluent comprising a second di-$C_{3+}$ olefin, a second ether, unreacted first olefin mixture, and unreacted second olefin mixture, wherein reacting the second mixture produces a greater amount, on a mole basis, of the second di-$C_{3+}$ olefin than the second ether;
combining the second effluent and a third process fluid to produce a third mixture, wherein the third process fluid comprises ≥1 wt. % of a second alcohol;
reacting the third mixture in a third reactor in the presence of a third catalyst to produce a third effluent comprising a third ether, a third di-$C_{3+}$ olefin, unreacted first olefin mixture, and unreacted second olefin mixture; and
separating a second product and a recycle from the third effluent, wherein the second product comprises at least a portion of any first di-$C_{3+}$ olefin, at least a portion of the second di-$C_{3+}$ olefin, and at least a portion of the third di-$C_{3+}$ olefin, wherein the recycle comprises at least a portion of the second ether and at least a portion of the third ether, and wherein the second process fluid comprises ≥1 wt. % of the recycle.

18. The process of claim 17, wherein separating the second product and the recycle from the third effluent comprises:
separating a second byproduct and a fourth effluent from the third effluent, wherein the second byproduct comprises at least a portion of the unreacted first olefin mixture and at least a portion of the unreacted second olefin mixture; and
separating the second product, the recycle, and a third product comprising one or more tri-$C_{3+}$ olefins from the fourth effluent.

19. The process of claim 17, wherein an amount of the second ether and the third ether in the second process fluid is ≥70 wt. % based on the weight of the second process fluid.

20. The process of claim 17, wherein the first product comprises >98 wt. % of methyl tert-butyl ether based on the weight of the first product.

21. The process of claim 17, wherein the first effluent comprises ≤0.1 wt. % of any first di-$C_{3+}$ olefin based on the weight of the first effluent, and wherein the second effluent comprises ≥8 wt. % of the second di-$C_3$+ olefin based on the weight of the second effluent.

22. The process of claim 17, wherein at least one of the first, second, and third catalyst comprises ≥95 wt. % of at least one first cation exchange resin based on the weight of the first catalyst, and wherein reacting the first mixture comprises heating the first mixture to a temperature of ≥30° C. under an absolute pressure of 10 bar to 20 bar.

23. The process of claim 17, wherein:
the first olefin mixture comprises ≥90 wt. % of one or more $C_4$ monoolefins based on the weight of the first olefin mixture,
the first process fluid comprises ≥65 wt. % of the first alcohol based on the weight of the first process fluid,
the second olefin mixture comprises ≥90 wt. % of one or more $C_4$ monoolefins based on the weight of the second olefin mixture,
the second process fluid comprises ≥90 wt. % of the second ether, the third ether, or a combined amount of the second ether and the third ether based on the weight of the second process fluid, and
the third process fluid comprises ≥65 wt. % of the second alcohol based on the weight of the third process fluid.

24. The process of claim 17, wherein:
the first olefin mixture and the second olefin mixture have substantially the same composition and further comprise but-1-ene, cis-β-butylene, trans-β-butylene, n-butane, or a mixture thereof,
the first alcohol and the second alcohol independently comprise methanol, ethanol, n-propanol, n-butanol, n-amylalcohol, or a mixture thereof,
any first di-$C_{3+}$ olefin, the second di-$C_{3+}$ olefin, and third di-$C_{3+}$ olefin each comprise diisobutylene, and
the first product comprises ≥98 wt. % of methyl tert-butyl ether based on the weight of the first product.

25. The process of claim 17, wherein the second by-product comprises no greater than 1 wt % of isobutylene, based on the total weight of the second byproduct.

26. The process of claim 25, wherein the recycle comprises about 75 wt. % to about 90 wt. % of methyl tert-butyl ether based on a total weight of the recycle.

27. A process for $C_{3+}$ monoolefin conversion, comprising:
separating a first olefin mixture and a second olefin mixture from a raffinate comprising a mixture of isobutylene, but-1-ene, cis-β-butylene, trans-β-butylene, n-butane, and isobutane, wherein the first olefin mixture and the second olefin mixture have substantially the same composition:
combining methanol with the first olefin mixture to produce a first mixture;
reacting the first mixture in the presence of a first catalyst comprising a first cation exchange resin to produce a first effluent comprising a first methyl tert-butyl ether and unreacted first olefin mixture, wherein the first effluent comprises <1 wt. % of any first diisobutylene or is free of any first diisobutylene:
separating a first product and a first byproduct from the first effluent, wherein the first product comprises ≥98 wt. % of the first methyl tert-butyl ether, and wherein the first byproduct comprises at least a portion of the unreacted first olefin mixture;
combining the second olefin mixture, the first byproduct, and a recycle comprising methyl tert-butyl ether to produce a second mixture;
reacting the second mixture in the presence of a second catalyst comprising a second cation exchange resin to produce a second effluent comprising a second methyl tert-butyl ether, a second diisobutylene, unreacted first olefin mixture, and unreacted second olefin mixture, wherein reacting the second mixture produces a greater amount, on a mole basis, of the second diisobutylene than the second methyl tert-butyl ether;
optionally combining methanol with the second effluent to produce a third reaction mixture;
reacting the second effluent or the third reaction mixture in a third reactor in the presence of a third catalyst comprising a third cation exchange resin to produce a third effluent;
separating a second byproduct from the third reactor and/or the third effluent, wherein the second byproduct comprises but-1-ene, cis-β-butylene, trans-β-butylene, n-butane, and isobutane;
obtaining a second product, a third product, and the recycle from the third effluent, wherein the second product comprises ≥60 wt. % of diisobutylene, and wherein the third product comprises oligomers of order 3 produced from one or more of isobutylene, bute-1-ene, cis-β-butylene, and trans-β-butylene.

28. The process of claim 27, wherein the second byproduct comprises no greater than 1 wt % of isobutylene, based on the total weight of the second byproduct.

29. The process of claim 28, wherein the recycle comprises about 75 wt. % to about 90 wt. % of methyl tert-butyl ether based on a total weight of the recycle.

30. The process of claim 27, wherein the third effluent further comprises unreacted second mixture; and the process further comprises:
separating the second byproduct comprising at least a portion of the unreacted second mixture and a fourth effluent from the third effluent; and
separating the second product, the third product, and the recycle from the fourth effluent.

* * * * *